United States Patent [19]

Phipps

[11] Patent Number: 5,084,008
[45] Date of Patent: Jan. 28, 1992

[54] IONTOPHORESIS ELECTRODE

[75] Inventor: Joseph B. Phipps, Plymouth, Minn.

[73] Assignee: Medtronic, Inc., Minneapolis, Minn.

[21] Appl. No.: 455,546

[22] Filed: Dec. 22, 1989

[51] Int. Cl.$^5$ ............................................. A61N 1/30
[52] U.S. Cl. ..................................... 604/20; 128/803; 29/825
[58] Field of Search .......................... 604/20; 128/803; 29/825

[56] References Cited

U.S. PATENT DOCUMENTS

| | | | |
|---|---|---|---|
| 3,964,477 | 6/1976 | Ellis et al. | 604/20 |
| 3,991,755 | 11/1976 | Vernon et al. | 604/20 |
| 4,058,127 | 11/1977 | Buchalter | 128/803 |
| 4,141,359 | 2/1979 | Jacobsen et al. | 604/20 |
| 4,215,696 | 8/1980 | Bremer et al. | 128/641 |
| 4,250,878 | 2/1981 | Jacobsen et al. | |
| 4,273,135 | 6/1981 | Larimore et al. | 128/640 |
| 4,292,968 | 10/1981 | Ellis | 604/20 |
| 4,383,529 | 5/1983 | Webster | 604/20 |
| 4,398,545 | 8/1983 | Wilson | 128/798 |
| 4,416,274 | 11/1983 | Jacobsen et al. | 604/20 |
| 4,474,570 | 10/1984 | Ariura et al. | 604/20 |
| 4,519,973 | 5/1985 | Cahalan et al. | 264/267 |
| 4,522,211 | 6/1985 | Bare et al. | 128/640 |
| 4,524,087 | 6/1985 | Engel | 427/2 |
| 4,526,176 | 7/1985 | Bremer et al. | 128/641 |
| 4,528,265 | 7/1985 | Becker | 435/172.1 |
| 4,570,637 | 2/1986 | Gomes et al. | 128/639 |
| 4,602,909 | 7/1986 | Csillik et al. | 604/20 |
| 4,640,689 | 2/1987 | Sibalis | 604/20 |
| 4,702,732 | 10/1987 | Powers et al. | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,886,489 | 12/1989 | Jacobsen et al. | 604/20 |
| 4,927,408 | 5/1990 | Haak et al. | 604/20 |

FOREIGN PATENT DOCUMENTS

| | | |
|---|---|---|
| 0182520 | 5/1986 | European Pat. Off. |
| WO87/04936 | 8/1987 | PCT Int'l Appl. |
| 410009 | 5/1934 | United Kingdom |

OTHER PUBLICATIONS

Article entitled "Acrylic Ion-Transfer Polymers", by Ballestrasse 35 al, published in the *Journal of the Electrochemical Society*, Nov., 1987, vol. 134, No. 11, pp. 2745-2749.

Article entitled "Essentials of Medical Electricity", by Cumberbach, Henry Kimpton (publisher), London, 1933, pp. 3-9.

Article entitled "Physical Therapy and Radiology", published in *Clinical Medicine and Surgery*, vol. 42, No. 8, 1935, pp. 386-389.

"Studies on Iontophoresis. I. Experimental Studies on the Causes and Prevention of Iontophoretic Burns", by Molitor, M.D. et al, *American Journal of Medical Science*, vol. 198:778-785, 1939.

Article "Pharmacologic Aspects of Drug Administration by Ion-Transfer", by Molitor, published in *The Merck Report*, pp. 22-29, Jan., 1943.

Abstract "Iontophoresis as a Potential Method of Insulin Administration", T. J. Petelenz et al, International Symposium on Artificial Organs, Biomedical Engineering and Transplantation, Jan. 20-23, 1986, Salt Lake City, Utah.

(List continued on next page.)

*Primary Examiner*—Lee S. Cohen
*Attorney, Agent, or Firm*—Daniel W. Latham

[57] ABSTRACT

An improved iontophoresis electrode employing a current distributing member and a drug reservoir containing an ionic drug. In direct or intimate contact with the current distribution member is a salt layer or ion source layer. In direct or intimate contact with the salt layer or ion source material is a size selective (i.e., a semipermeable membrane) or a material selective for ions having a charge opposite to the charge of the ionic drug which is to be delivered (i.e., a charge selective mebmrane). The current distribution member is separated from the drug reservoir by means of the salt layer and the membrane.

15 Claims, 1 Drawing Sheet

Abstract "Evaluation of Transdermal Iontophoretic Drug Delivery", J. B. Phipps et al, International Symposium on Artificial Organs, Biomedical Engineering and Transplantation, Jan. 20–23, 1986, Salt Lake City, Utah.

Poster presentation "Evaluation of Transdermal Iontophoretic Drug Delivery", J. B. Phipps et al, International Symposium on Artificial Organs, Biomedical Engineering and Transplantation, Jan. 20–23, 1986, Salt Lake City, Utah.

Reference entitled "Principles of Polymer Systems", by F. Rodriguez, McGraw-Hill Book Co., 1970, pp. 382–390.

Article entitled "Noninvasive Delivery of a Novel Inotropic Catecholamine: Iontophoretic Versus Intravenous Infusion in Dogs", by John E. Sanderson et al published in the *Journal of Pharmaceutical Sciences*, vol. 76, No. 3, pp. 215–218, Mar., 1987.

Excerpt, *Corrosion and Corrosion Control*, third edition, 1985, Uhlig et al, pp. 27–29, 217–221.

IONTOPHORESIS ELECTRODE

REFERENCE TO RELATED APPLICATIONS

Reference is made to commonly assigned U.S. patent application entitled "IONTOPHORESIS ELECTRODE", filed Oct. 28, 1988, Ser. No. 264,238, by Untereker et al, abandoned, and to applicant's commonly assigned application, Ser. No. 264,239, entitled "IONTOPHORESIS ELECTRODE" also filed Oct. 28, 1988, abandoned. These applications are hereby incorporated by reference in their entirety. Reference also is made to previously filed, commonly assigned U.S. patent application Ser. No. 154,566 entitled "IONTOPHORETIC DRUG DELIVERY", filed Feb. 10, 1988, by Untereker et al.

BACKGROUND OF THE INVENTION

This invention relates to methods and apparatus for transdermal medicament delivery and to improvements therein. More specifically, this invention relates to improved methods and apparatus for active (as opposed to passive) transdermal, ambulatory drug delivery. Yet more particularly, this invention relates to increasing the efficiency of iontophoresis devices and to improved methods of making and using such devices.

Iontophoresis, according to *Dorland's Illustrated Medical Dictionary*, is defined to be "the introduction, by means of electric current, of ions of soluble salts into the tissues of the body for therapeutic purposes." Iontophoretic devices have been known since the early 1900's. British patent specification 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming from the electrodes and the material containing the medicament or drug to be delivered transdermally, a galvanic cell which itself produced the current necessary for iontphoretically delivering the medicament. This ambulatory device thus permitted iontophoretic drug delivery with substantially less interference with the patient's daily occupation.

Recently, there has been considerable interest in iontophoresis. Iontophoresis has been found to be useful in the transdermal administration or introduction of lidocaine hydrochloride, hydrocortisone, acetic acid, flouride, penicillin, dexamethasone sodium phosphate, and many other drugs. Perhaps the widest use of iontophoresis is to induce sweating by the iontophoretic delivery of pilocarpine nitrate into the skin. The sweat so produced is analyzed in a screening procedure for the detection of cystic fibrosis.

In presently known iontophoresis devices, at least two electrodes are used. Both these electrodes are disposed so as to be in intimate electrical contact or electrical communication with some portion of the skin. The "active" electrode is the electrode from which the ionic drug is delivered into the body. The "indifferent" ground or counter electrode serves to close the electrical circuit through the body. A battery or other current source is coupled to the electrode to provide the electromotive force (i.e., repulsion) to drive the drug into the body. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the indifferent electrode. Of course, simultaneous delivery of drugs from both of the electrodes is also possible.

Generally, iontophoresis electrodes include a reservoir of the drug, typically incorporated in the form of a salt of the drug, for example a fluoride or sulfate. These reservoirs may take the form of preformed gel bodies, such as disclosed in U.S. Pat. No. 4,382,529 issued to Webster, solid adhesive bodies as disclosed in U.S. Pat. No. 4,416,274, issued to Jacobson, or fluid reservoirs as disclosed in U.S. Pat. No. 4,250,878, issued to Jacobsen. Electrical current is typically applied to the fluid reservoir by means of a current distributing member, which may take the form of a metal plate, a foil layer, a conductive screen, or a dispersion of conductive particles within the drug reservoir.

Typically, the current distributing member in iontophoresis electrodes has been constructed of an inert material, such as stainless steel or platinum. However, more recently use of sacrificial current distributing members which are themselves oxidized or reduced during delivery of the drug has been discussed. Use of sacrificial current distributing members can avoid the pH changes and other adverse effects associated with the hydrolysis of water which generally accompanies the use of inert current distributing members. Electrodes with sacrificial current distributing members are disclosed in U.S. Pat. No. 4,744,787, issued to Phipps et al, incorporated herein by reference in its entirety. Such electrodes are also discussed in the above-cited copending application by Untereker et al, also incorporated herein by reference in its entirety.

In this patent and copending application, the drug reservoir contains a counter ion which reacts with the electrochemically-generated ion from the sacrificial current distributing member to form a neutral or substantially insoluble compound. Preferably, the counter ion in the drug reservoir is provided by the drug salt. However, many drug salts do not possess the proper counter ion to effectively react with the electrochemically-generated ion. For example, use of a drug salt having only a nitrate counter ion would be difficult to use with a silver anode since the compound formed in the drug reservoir, silver nitrate, is water soluble. The addition of a nondrug salt (e.g., NaCl) can be made to the drug reservoir to provide the proper counter ion (e.g., $Cl^-$) for use with, a particular sacrificial electrode (e.g., Ag). This approach produces extraneous nondrug coions (e.g., $Na^+$) which can effectively compete with drug ion delivery to the skin. Thus, the efficiency of the iontophoresis device may be reduced.

An alternative approach to avoiding the adverse effects associated with hydrolysis of water at the current distributing member is disclosed in the published PCT patent application Ser. No. WO 87/04936, published Aug. 27, 1987, by Sanderson et al, corresponding to U.S. Pat. No. 4,722,726. This electrode system is also described in the article "Noninvasive Delivery of a Novel Ionotropic Catecholamine: Iontophoretic Versus Intravenous Infusion in Dogs" by Sanderson et al, published in the *Journal of Pharmaceutical Sciences*, Vol. 76, No. 3, March 1987, pp. 215-218. In this electrode system, an inert current distributing member is used and the electrode is divided into an upper chamber filled with a buffer and a lower chamber containing the ionic drug. The upper chamber is spacially separated from the lower chamber by an ion mobility inhibiting means such as an ion exchange membrane. As described, it is apparent that Sanderson et al intend that a buffer solution in the upper chamber be used to mitigate the effects of hydrolysis of water, and that the ion selective membrane isolate the drug from the contents of the upper chamber. The lower chamber of Sanderson et al includes a microporous membrane which permits electrical migration of ions (from the chamber to the skin) but which inhibits leakage of fluid from the device.

There are two disadvantages of the Sanderson et al device. First, use of this invention is practically restricted to devices using electrodes which generate $H^+$ or $OH^-$ ions since buffering agents generally do not form neutral, insoluble products with other ions, e.g., $Ag^+$ or $Sn^{++}$ as would be electrochemically-generated ions from silver or tin electrodes respectively. Second, the solution or gel used to contain the buffering agents in Sanderson et al are susceptible to dry-out or other changes in physical properties during storage and use.

In electrodes including fluid reservoirs, as disclosed in U.S. Pat. No. 4,250,878 issued to Jacobson, delivery of the drug typically takes place through a microporous membrane. Typically, such membranes are permeable based on size, and therefore must be permeable to any ion equal to or smaller than the drug ion intended to be delivered. In U.S. Pat. No. 4,640,689, issued on Feb. 3, 1987 to Sibalis, an iontophoresis electrode including a gel type drug reservoir provided with a semipermeable membrane is disclosed. This reference also suggests the use of an "ion selective retention gel" intermediate the drug reservoir and the semipermeable membrane. The ion to be retained by the gel is not discussed.

Commonly owned pending application, Ser. No. 264,239, supra, discloses the use of a layer of charge selective material applied to the surface of the current distributing member to prevent electrochemically generated ions from migrating into the drug reservoir. The counter ion of the ionomer of the coating, e.g., $Cl^-$, can be used to react with the electrochemically generated ion from the current distributing member, e.g., $Ag^+$, to form an insoluble product, e.g., AgCl. In addition, the drug counter ion, e.g., $Cl^-$, can migrate through the coating and react with the electrochemically generated species, e.g., $Ag^+$. However, in some applications, the type or quantity of ion available from the charge selective membrane and the drug reservoir may not be sufficient to prevent the migration of electrochemically generated ions, particularly at high currents or long durations of use.

SUMMARY OF THE INVENTION

The present invention relates to an improvement to iontophoresis electrodes. The invention is especially beneficial when embodied in iontophoresis electrodes of the type employing sacrificial cathodes or anodes which are oxidized or reduced, respectively, during iontophoretic drug delivery. The use of such sacrificial current distributing members substantially avoids electrolysis of water, as the materials chosen for the current distributing members are oxidized or reduced at a lower voltage than required to cause significant hydrolysis of water. For example, the positive electrode (anode) may be silver and the negative electrode (cathode) may be silver/silver chloride.

In cases where the type or quantity of counter ions provided by the charge selective material, and the type or quantity of counter ions provided by the drug reservoir are insufficient to prevent migration of electrochemically-generated ions (e.g., $Ag^+$) from the electrode (e.g., silver) into the drug reservoir, an ion source layer containing a sufficient quantity of appropriate counter ions would be beneficial. The type of counter ion provided by the ion source layer (e.g., $Cl^-$) would be those which react with the electrochemically-generated ion of the current distributing member (e.g., $Ag^+$). The quantity of counter ion provided by the ion source layer would be sufficient to substantially prevent migration of electrochemically-generated ions into the drug reservoir. The quantity of counter ion provided by the ion source layer in the practice of this invention would increase with the iontophoretic current or the duration of iontophoretic drug delivery.

Briefly, in one aspect, the present invention is an electrode for an iontophoresis device comprising:
 a conductive, current distributing member;
 means for coupling said current distributing member to a source of electrical current; a reservoir containing an ionic or ionizable drug to be delivered;
 an ion source layer in intimate contact with said current distributing member; and
 a layer of selectively permeable material applied to said ion source layer and which is intermediate said current distributing member and said reservoir.

As sometimes used herein, the term "selectively permeable material" is intended to include charge selective as well as size selective materials. In a preferred practice of this aspect of this invention the selectively permeable material is charge selective.

In another aspect, the present invention is an iontophoresis electrode, comprising:
 a current distributing member fabricated of a material which is readily oxidized or reduced at a voltage less than the voltage required to cause significant hydrolysis of water;
 connector means for connecting said current distributing member to a source of electrical current;
 reservoir means electrically coupled to said current distributing member, said reservoir means containing an ionic drug;
 an ion source layer in intimate contact with said current distributing member, said ion source layer containing a substance which interacts with ions electrochemically generated from the sacrificial electrode (e.g., the current distribution member) to produce a product which is substantially immobile within said reservoir; and
 a layer of charge selective material applied to said ion source layer, said material selective for ions of opposite charge as said ionic drug, said material applied intermediate said current distributing member and said reservoir means.

In a preferred practice of this aspect of the invention the reservoir means is compounded or constructed with a counter ion which reacts with the oxidation or reduction product of the current distribution member to produce a species which is substantially insoluble within said reservoir.

In yet another aspect, this invention is a method of fabricating an iontophoresis electrode, comprising the steps of:
 selecting an ionic or ionizable drug to be delivered;

including said drug within a reservoir through which said drug is permeable;
selecting a conductive current distributing member;
selecting an ion source material;
selecting a selectively permeable material, e.g., a material which is a charge selective material selectively permeable to ions of the charge opposite to that of said drug; and
assembling said electrode by applying the ion source material and then said selectively permeable material to said current distributing member and mounting said current distributing member to said reservoir such that said material is located intermediate said current distributing member and said reservoir.

In yet another aspect, the present invention is a method of fabricating an iontophoresis electrode, comprising the steps of:
selecting an ionic drug to be delivered;
selecting a sacrificial current distributing member fabricated of a material readily oxidized or reduced at a voltage less than the voltage required to cause significant hydrolysis of water;
applying an ion source material to said current distributing member with a counter ion which will react with a species electrochemically generated from the sacrificial electrode to produce a neutral product or a product which is substantially insoluble in said reservoir; and
applying a selectively permeable material to said current distributing member, said material being permeable to ions having a charge opposite to the charge of said ionic drug, said material applied between said current distributing member and said reservoir.

In a preferred practice, this method includes the step of compounding said ionic drug with a counter ion which will react with the material of which said current distributing member is fabricated, after said material is oxidized or reduced, to form a neutral compound, and placing said compounded ionic drug into a reservoir through which said ionic drug is permeable.

DETAILED DESCRIPTION OF THE INVENTION

Figure 1:
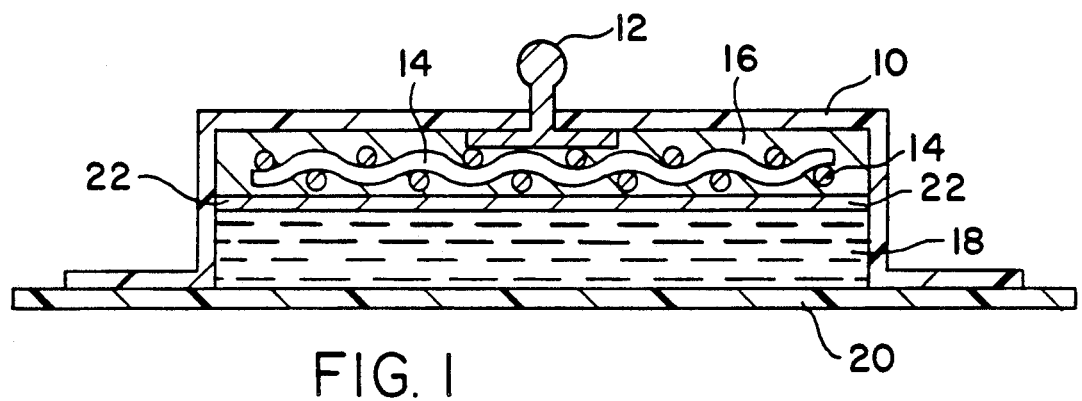
FIG. 1 shows a sectional view through an electrode according to the present invention.

FIG. 1 shows a sectional view through an active iontophoresis electrode according to the present invention. The electrode is provided with a housing 10, which may be fabricated of an insulative plastic, such as polyvinyl chloride or polyethylene. An electrical snap connector 12 extends from the top side of housing 10, and is electrically coupled to a screen 14 which serves as the current distribution member. Reservoir 18 contains the drug to be delivered which typically is either ionic drug or is readily ionizable within the reservoir. Screen 14 is preferably fabricated of a material which is reduced or oxidized at an electrical potential less than that required to cause significant hydrolysis of water. Suitable examples are silver for the positive electrodes (anodes) and silver/silver chloride for the negative electrodes (cathodes).

Surrounding screen current distribution member 14 and in direct, intimate contact therewith is a salt layer, an ion layer or an ion source material 16. For example, if the current distribution member 14 were a silver anode, then the ion source layer could contain chloride ion provided by potassium chloride or sodium chloride dissolved or dissolvable within the ion source layer. During iontophoresis, silver ion electrochemically-generated by the anode would react with chloride ion of the ion source layer to form substantially insoluble silver chloride. If the current distribution member 14 were a silver/silver chloride cathode, then the ion source layer could contain silver ion provided by silver nitrate or silver acetate dissolved or dissolvable within the ion source layer. During iontophoresis, chloride ion electrochemically-generated by the cathode, would react with silver ion provided by the ion source layer.

In principle, the ion source layer can contain any ingredient which substantially eliminates migration of electrochemically-generated ions into the drug reservoir. This can be achieved by the formation of neutral or substantially insoluble compounds by reaction between the electrochemically-generated ions and the ion source layer.

In a preferred embodiment, the cation of the ion source layer when the current distribution member is an anode, or the anion of the ion source layer when the current distribution member is a cathode, would have limited mobility through the charge or size selective membrane. Larger biocompatible organic ions such as vitamin B1, B6, acetate or citrate are examples of such preferred cations and anions.

The ion source layer could be composed of an appropriate salt fully or partially dissolved in a thin hydrogel material. Alternatively, the ion source layer could be fabricated as a substantially dehydrated layer (e.g., NaCl) which would absorb a solvent (e.g., $H_2O$, ethanol) from the drug reservoir prior to or during iontophoresis, thus becoming conductive. The ion source layer could also be composed of material which effectively captures the electrochemically-generated ion, such as an ion exchange resin or chelating agent (e.g., EDTA).

Overlying salt layer 16 is a selectively permeable material 22 which, in this embodiment, is permeable to ions having a charge opposite that of the drug in reservoir 18. For example, if the electrode is a positive electrode used to deliver a positively charged drug, material 22 would be an anion selective material or a size selective material which limits the permeability of the cations of the ion source material 22 or drug reservoir 18. Conversely, if the electrode of FIG. 1 is the negative electrode, used to deliver a negatively charged drug, material 22 would be a cation selective material or a size selective material which limits the permeability of the anions of the ion source material 22 or drug reservoir 18.

Examples of anionic and cationic selective membranes are described in the article "Acrylic Ion-Transfer Polymers", by Ballestrasse et al, published in the *Journal of the Electrochemical Society*, November 1987, Vol. 134, No. 11, pages 2745-2749. An additional appropriate anion exchange membrane would be a copolymer of styrene and divinyl benzene reacted with trimethylamine to provide an anion exchange membrane (see "Principles of Polymer Systems", by F. Rodriguez, *McGraw-Hill Book Co.*, 1979, pages 382-390). These articles are incorporated herein by reference in their entirety. An additional appropriate cationic permeable membrane for use in conjunction with delivery of a positively charged drug would be a sulfonated styrene polymer or a sulfonated fluorocarbon polymer, e.g. Nafion TM membranes, a product of DuPont.

Examples of size selective materials are those classified as semipermeable such as dialysis membranes (e.g., cellulosic materials) or polycarbonate microporous membranes (e.g., Nucleopore TM).

The provision of coating 22 has several important benefits. First, it minimizes interaction of the ionic drug and the current distribution member during iontophoresis and storage. This is believed beneficial in extending the shelf life of iontophoresis electrodes and makes possible combinations of drugs and current distribution members which might otherwise not provide an appropriate shelf life.

In the context of shelf life, providing the anion selective material 22 in direct contact (via the salt layer 16) with the current distribution member 14 is especially important. Although anion selective materials as discussed above select for negatively charged ions, positively charged ions will diffuse through them, over time, given the presence of a concentration gradient across the material. For example, the above cited Sanderson references suggest construction of an iontophoresis electrode in two chambers, the upper chamber containing the current distribution member being filled with a buffer solution, the lower chamber being filled with a drug solution, and an anion selective membrane provided intermediate the upper and lower chambers. Diffusion of positive ions from both the upper buffer chamber and the lower drug chamber would occur across the anion selective membrane would occur at a sufficient rate to significantly limit the shelf life of such an electrode. This may require that the electrode be assembled shortly before use.

Because the electrode according to the present invention provides a charge selective material 22 directly applied to the salt layer or ion source material 16 which is itself directly applied to the current distributing member, the quantity of drug ions which diffuse across the material is significantly reduced due to the limited volume present near the current distributing member. This allows for the electrode to be constructed in advance, while providing an extended shelf life.

In embodiments employing a sacrificial current distribution member, the provision of an ion source material and a selectively permeable membrane is particularly advantageous. In use, a source of electrical current will be coupled to snap connector 12, and thereby to screen 14. Typically, such power supplies are constant current power supplies, and the voltage differential between screen 14 and ion source material 16 will thereby be determined by the voltage differential required to reduce or oxidize the material of screen 14 in the presence of the ion source material 16.

If the drug to be delivered is a positive drug, for example, hydromorphone, screen 14 would be fabricated of a readily oxidizable material such as silver, and the ion source material 16 would contain or possess a counter ion which reacts with ionic silver to form a substantially insoluble or neutral compound. For example, ion source material 16 may contain chloride ion. When coupled to the power supply, screen 14 will be oxidized to produce silver ions. However, ion source material 16 will substantially reduce the migration of silver ions into the reservoir 18. Instead, chloride ions will react to form a silver chloride precipitate at the screen. This prevents migration of silver ions into the drug reservoir. This embodiment is particularly advantageous when employed with drug salts which do not have the proper counter ion to react with electrochemically-generated ions. In this example, the selectively permeable membrane would be an anionic selective membrane or a size selective material which limits the permeability of cations.

If the drug to be delivered is a negatively charged ion, screen 14 would be fabricated of a readily reducible material, such as silver/silver chloride. Or in this case, material 22 would be a cationic selective material or a size selective material which limits the permeability of anions. The ion source material 16 would contain a counter ion which forms a substantially insoluble or neutral compound when reacted with the electrochemically-generated ion (e.g., $Cl^-$). An example of an appropriate ion source material for use with a silver/silver chloride cathode would be a material containing silver acetate. In use, ionic silver in the silver chloride portion of screen 14 would be reduced, producing mobile chlorine ions. Ion source material 16 would substantially reduce migration of chlorine ions into reservoir 18. Positively charged silver ions from the ion source material 16 would react with electrochemically-generated chloride ions to form a substantially insoluble silver chloride precipitate at or near screen 14. The free acetate ions in the ion source material 16 are hindered from migrating into the drug reservoir 18 by the selectively permeable membrane 22.

This electrode construction provides significant additional advantages over prior art iontophoresis electrodes. For example, this construction reduces any toxic effects associated with the use of a silver current distribution member, and may make possible the use of materials such as a lead, which would otherwise be counterindicated. In addition, it allows the use of materials for current distribution member 14 which in their ionized state might otherwise react with the ionic drug in reservoir 18 during use of the electrode. In addition, this electrode construction allows use of drug salts with a wider variety of counter ions, since the ion source material is composed of an ion which reacts with the electrochemically-generated ions from the sacrificial current distribution member.

As manufactured, it is anticipated that the drug reservoir 18 will take the form of a solid or semisolid gel. In this case, the release liner 20 would typically be provided to seal the drug reservoir 18 against contamination and to prevent the gel in reservoir 18 from drying out over time. Alternative embodiments of the invention may employ fluid drug reservoirs surrounded by semipermeable membranes.

Preferably, drug reservoir 18 is free of ionic or readily ionizable material other than the drug to be delivered. For example, the matrix may take the form of a polar, nonionic gel, such as a polyvinyl alcohol gel or a gel as disclosed in EPO Patent No. 0 060 451, issued on Sept. 17, 1986 to Lattin et al. This EPO patent is incorporated by reference herein in its entirety.

Figure 2:
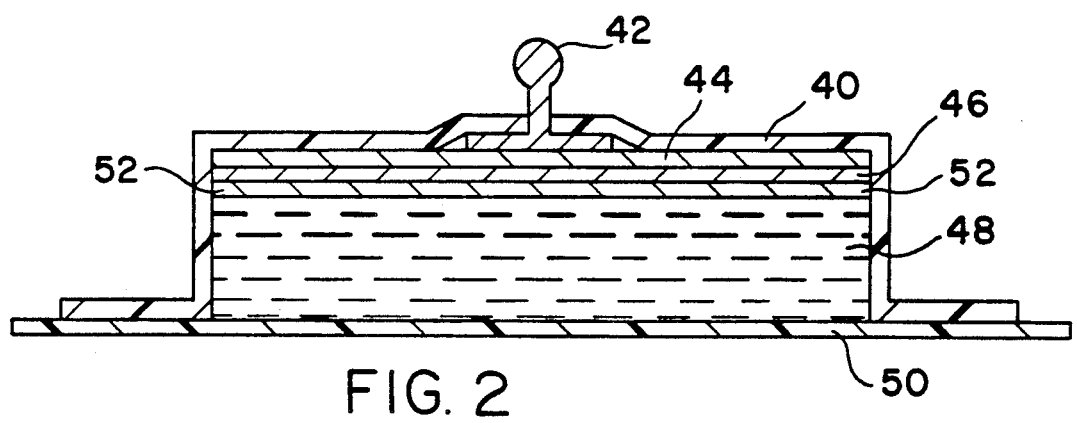
FIG. 2 shows a sectional view through a second embodiment of an electrode according to the present invention.

FIG. 2 is a sectional view of an alternative embodiment of an iontophoresis electrode according to the present invention. The electrode is provided with a housing 40, which may be fabricated of an insulative plastic, such as polyvinyl chloride or polyethylene. An electrical snap connector 42 extends from the top side of housing 40, and is electrically coupled to metallic foil 44 which serves as a current distribution member. Foil 44 my be fabricated of a material such as silver or silver chloride which is reduced or oxidized at an electrical potential less than the potential required to cause significant hydrolysis of water. A salt or ion layer 46 is applied as a coating or layered directly over foil 44, and serves the same function as the salt layer 16. Selectively permeable (i.e., ion selective) material 52 is applied directly over and in contact with salt layer or ion source layer 46. Selectively permeable (i.e., ion selective) material 52 serves the same function in this embodiment of the invention as discussed in conjunction with FIG. 1. The iontophoretic drug for delivery is contained within reservoir 48, which will take the form of a solid or semisolid gel in the preferred embodiment. A release liner 50 is provided to seal the drug reservoir 48 against contamination and to prevent the reservoir 18 from drying out over time.

It is to be noted that, depending upon context, the term "electrode" has at least two interpretations. "Electrode" can mean the one of the two assemblies (i.e., "active electrode" and "indifferent electrode") which are in contact with a patient's skin in an iontophoresis device. "Electrode" is also sometimes used to mean the portion of assembly in electrical contact with, e.g., the reservoir. "Electrode" in this sense could comprise a snap and electrically coupled current distribution member.

An electrode according to the present invention also may employ a selectively permeable, e.g., an ion selective material, membrane at the interface of the drug reservoir and the skin, as disclosed in the above cited patent application entitled "IONTOPHORESIS ELECTRODE" by Untereker et al. In such case, the membrane applied between the reservoir and the skin would selectively pass ions having the charge of the ionic drug to be delivered.

What is claimed is as follows:

1. An iontophoresis electrode, comprising:
   a current distributing member comprised of a material which is readily oxidized or reduced at a voltage less than the voltage required to cause significant hydrolysis of water;
   connector means for electrically connecting said current distributing member to a source of electrical current;
   reservoir means electrically connected to said current distributing member said reservoir means containing an ionic or ionizable drug;
   an ion source layer in intimate contact with said current distributing member, said ion source layer containing a substance which interacts with a species electrochemically generated from the current distributing member to produce a product which is substantially immobile;
   a layer of selectively permeable material applied to said ion source layer, said material selective for ions of the opposite charge as said ionic drug, said material applied intermediate said current distributing member and said reservoir means.

2. An electrode of claim 1 wherein the reservoir means contains a counter ion which reacts with an ion produced when said current distributing member is oxidized or reduced to produce a neutral or substantially insoluble compound within said reservoir.

3. The iontophoresis electrode of claim 1, wherein the current distributing member is comprised of silver.

4. The iontophoresis electrode of claim 3, wherein the substance contained in the ion source layer comprises chloride ions and the substantially immobile product comprises silver chloride.

5. The iontophoresis electrode of claim 1, wherein the current distributing member is comprised of silver chloride.

6. The iontophoresis electrode of claim 5, wherein the substance contained in the ion source comprises silver ions and the substantially immobile produce comprises silver chloride.

7. The iontophoresis electrode of claim 1, wherein the ion source layer contains cations and anions.

8. The iontophoresis electrode of claim 7, wherein the electrode is a cathode and the anions are selected from the group consisting of citrate and acetate.

9. The iontophoresis electrode of claim 7, wherein the electrode is a anode and the cations are selected from the group consisting of vitamin $B_1$ and vitamin $B_6$.

10. The iontophoresis electrode of claim 1, wherein the ion source layer comprises a salt at least partially dissolved in a hydrogel.

11. The iontophoresis electrode of claim 1, wherein the ion source layer contains an ion exchange resin or a chelating agent.

12. The iontophoresis electrode of claim 1, wherein the layer of selectively permeable material comprises an ion exchange membrane.

13. The iontophoresis electrode of claim 1, wherein the layer of selectively permeable material comprises a size selective material selected from the group consisting of semipermeable and microporous membranes.

14. A method of fabricating an iontophoresis electrode, comprising the steps of:
   selecting an ionic drug to be delivered;
   including said drug within a reservoir through which said drug is permeable;
   selecting a sacrificial current distributing member comprised of a material readily oxidizable or reduced by application of a voltage less than required to cause significant hydrolysis of water;
   selecting an ion source layer with a counter ion which will react with the material of which said current distributing member is comprised, after said material is oxidized or reduced, to form a neutral or substantially immobile compound;
   applying said ion source layer to said current distributing member; and
   applying a charge selective material to said ion source layer, said charge selective material permeable to ions having a charge opposite to the charge of said ionic drug, said charge selective material applied between said current distributing member and said reservoir.

15. A method of fabricating an iontophoresis electrode, comprising the steps of:
   selecting an ionic drug to be delivered;
   including said drug within a reservoir through which said drug is permeable;
   selecting a sacrificial current distributing member comprised of a material readily oxidizable or reduced by application of a voltage less than required to cause significant hydrolysis of water;
   selecting an ion source layer with a counter ion which will react with the material of which said current distributing member is comprised, after said material is oxidized or reduced, to form a neutral or substantially immobile compound;

selecting a charge selective material, said charge selective material being permeable to ions having a charge opposite to the charge of said ionic drug; and assembling said electrode by arranging said ion source layer and said charge selective material between said current distributing member and said reservoir such that said ion source layer and said charge selective material are located intermediate thereof, said ion source layer being in contact with said current distributing member and said charge selective material being in contact with said reservoir.

* * * * *